United States Patent
Karason

(10) Patent No.: US 7,107,180 B2
(45) Date of Patent: Sep. 12, 2006

(54) METHOD AND SYSTEM FOR DETERMINING AN ACTIVITY LEVEL IN AN INDIVIDUAL

(75) Inventor: Gudjon G. Karason, Sollentuna (SE)

(73) Assignee: Ossur hf, Reykjavik (IS)

( * ) Notice: Subject to any disclaimer, the term of this patent is extended or adjusted under 35 U.S.C. 154(b) by 153 days.

(21) Appl. No.: 10/986,303

(22) Filed: Nov. 12, 2004

(65) Prior Publication Data
US 2005/0103129 A1 May 19, 2005

Related U.S. Application Data

(60) Provisional application No. 60/519,623, filed on Nov. 14, 2003.

(51) Int. Cl.
*G06F 15/00* (2006.01)

(52) U.S. Cl. ................................ 702/160; 702/189

(58) Field of Classification Search ............. 702/160, 702/182–185, 189
See application file for complete search history.

(56) References Cited

U.S. PATENT DOCUMENTS

| | | | |
|---|---|---|---|
| 5,375,610 A | 12/1994 | LaCourse et al. | |
| 5,788,655 A | 8/1998 | Yoshimura et al. | |
| 5,989,200 A | 11/1999 | Yoshimura et al. | |
| 6,159,130 A | 12/2000 | Torvinen | |
| 6,498,994 B1 | 12/2002 | Vock et al. | |
| 6,513,381 B1 | 2/2003 | Fyfe et al. | |
| 6,516,289 B1 | 2/2003 | David | |
| 6,527,715 B1 | 3/2003 | Balkin et al. | |
| 6,546,134 B1 | 4/2003 | Shrairman et al. | |
| 6,551,252 B1 | 4/2003 | Sackner et al. | |
| 6,588,423 B1 | 7/2003 | Sinderby | |
| 6,589,190 B1 | 7/2003 | Kanderian, Jr. et al. | |
| 6,605,038 B1 | 8/2003 | Teller et al. | |
| 6,607,484 B1 | 8/2003 | Suzuki et al. | |
| 6,876,947 B1 * | 4/2005 | Darley et al. ............. 702/160 |
| 2001/0029319 A1 | 10/2001 | Kazlausky et al. | |
| 2003/0114736 A1 | 6/2003 | Reed et al. | |

FOREIGN PATENT DOCUMENTS

| | | |
|---|---|---|
| EP | 0 791 328 A1 | 8/1997 |
| EP | 0 797 169 A1 | 9/1997 |
| EP | 1 195 135 A2 | 4/2002 |
| WO | WO 81/01506 | 6/1981 |

OTHER PUBLICATIONS

Gildenhuys et al., *Accuracy of AMP 331 Using a Scripted Test Protocol*.

(Continued)

*Primary Examiner*—Edward Raymond
(74) *Attorney, Agent, or Firm*—Bacon & Thomas

(57) ABSTRACT

A method for quantifying activity levels of an individual within a predetermined time period including measuring a plurality of activity variables from an individual during a predetermined time period, providing a plurality of activity variables with minimum and maximum threshold values and a weighing factor, calculating a subindex for each of the activity variables as a function of the minimum and maximum threshold values and the weighing factor, and calculating a sum of the activity variables to determine an activity index of an individual. A personal activity level analysis system is configured to execute the method for obtaining an activity index used in quantifying an activity level of an individual.

11 Claims, 3 Drawing Sheets

OTHER PUBLICATIONS

*Dynastream's Patented SpeedMax Technology For Accurate Monitoring of Physical Activity Levels*, White Paper, May 2003.
AMP 331 Advanced Activity Monitoring With A Measurable Difference, downloaded from http://www.dynastream.com/products/amp331/ on Nov. 11, 2003.
Product Specification—AMP 331.

Coleman et al., *Step activity monitor: long-term, continuous recording of ambulatory function*, Journal of Rehabilitation Research and Development vol. 36 No. 1, Jan. 1999.
Hartsell, et al., *Accuracy of a custom-designed activity monitor: Implications for diabetic foot ulcer healing*, Journal of Rehabilitation Research and Development vol. 39 No. 3, May/Jun. 2002.

* cited by examiner

Above the Knee Amputees

| Variable | Variable name and Unit | Min | Max | Weighing Factor | Individual 1 Low Activity | | Individual 2 Medium Activity | | Individual 4 High Activity | |
|---|---|---|---|---|---|---|---|---|---|---|
| | | | | | Data | Result | Data | Result | Data | Result |
| Var1 | Total time spent in Active class [min/day]: | 0 | 120 | 10 | 18 | 1.5 | 23 | 1.9 | 70.5 | 5.9 |
| Var2 | Total time spent in Locomotion class [min/day]: | 0 | 60 | 10 | 3 | 0.5 | 7 | 1.2 | 25 | 4.2 |
| Var3 | Total number of strides: | 0 | 10000 | 10 | 1487 | 1.5 | 3403 | 3.4 | 11310 | 10.0 |
| Var4 | Total distance traveled [m]: | 0 | 10000 | 10 | 347 | 0.3 | 1758 | 1.8 | 6932 | 6.9 |
| Var5 | Mean speed [m/s]: | 0.5 | 1.5 | 10 | 0.6 | 1.0 | 1.06 | 5.6 | 1.17 | 6.7 |
| Var6 | Mean cadence [strides/min]: | 30 | 60 | 10 | 36.4 | 2.1 | 50.1 | 6.7 | 55.68 | 8.6 |
| Var7 | Number of walking streaks: | 20 | 150 | 10 | 25 | 0.4 | 64 | 3.4 | 145 | 9.6 |
| Var8 | Maximun sustained walking speed [m/s]: | 0.5 | 3 | 10 | 0.9 | 1.6 | 2.14 | 6.6 | 1.64 | 4.6 |
| Var9 | Longest period of locomotion [min]: | 0 | 10 | 10 | 0.8 | 0.8 | 1.5 | 1.5 | 5.3 | 5.3 |
| Var10 | Longest consecutive distance [m]: | 0 | 1000 | 10 | 40 | 0.4 | 118 | 1.2 | 419 | 4.2 |
| | ACTIVITY INDEX | | | | | 10.2 | | 33.2 | | 65.9 |

FIG.2

Below the Knee Amputees

| Variable | Variable name and Unit | Min | Max | Weighing Factor | Individual 4 Low Activity | | Individual 5 Medium Activity | | Individual 6 High Activity | |
|---|---|---|---|---|---|---|---|---|---|---|
| | | | | | Data | Result | Data | Result | Data | Result |
| Var1 | Total time spent in Active class [min/day]: | 0 | 120 | 10 | 30.5 | 2.5 | 56 | 4.7 | 155 | 10.0 |
| Var2 | Total time spent in Locomotion class [min/day]: | 0 | 60 | 10 | 10.4 | 1.7 | 9.4 | 1.6 | 75 | 10.0 |
| Var3 | Total number of strides: | 0 | 10000 | 10 | 3312 | 3.3 | 6281 | 6.3 | 23464 | 10.0 |
| Var4 | Total distance traveled [m]: | 0 | 10000 | 10 | 947 | 0.9 | 2177 | 2.2 | 16728 | 10.0 |
| Var5 | Mean speed [m/s]: | 0.5 | 1.5 | 10 | 0.5 | 0.0 | 0.97 | 4.7 | 1.23 | 7.3 |
| Var6 | Mean cadence [strides/min]: | 30 | 60 | 10 | 39.69 | 3.2 | 50.6 | 6.9 | 53.1 | 7.7 |
| Var7 | Number of walking streaks: | 20 | 150 | 10 | 63 | 3.3 | 118 | 7.5 | 262 | 10.0 |
| Var8 | Maximun sustained walking speed [m/s]: | 0.5 | 3 | 10 | 0.8 | 1.2 | 1.48 | 3.9 | 2.3 | 7.2 |
| Var9 | Longest period of locomotion [min]: | 0 | 10 | 10 | 2 | 2.0 | 1 | 1.0 | 8 | 8.0 |
| Var10 | Longest consecutive distance [m]: | 0 | 1000 | 10 | 64 | 0.6 | 53 | 0.5 | 638 | 6.4 |
| | ACTIVITY INDEX | | | | | 18.9 | | 39.2 | | 86.6 |

FIG.3

METHOD AND SYSTEM FOR DETERMINING AN ACTIVITY LEVEL IN AN INDIVIDUAL

This application claims the benefit of U.S. Provisional Application No. 60/519,623 filed Nov. 14, 2003.

BACKGROUND

In many areas of research, medicine, physical training and rehabilitation, objective data describing an individual's ambulatory function is a useful indication of the individual's condition. Typically, information is obtained from an individual regarding their habits and abilities, and a subjective evaluation is conducted by a healthcare professional to assess the activity level of an individual. While such subjective evaluations are quick and inexpensive, the inherent subjectivity may lead to biased and inaccurate results.

Another approach comprises obtaining objective detailed measurements over short periods of time within a controlled laboratory setting. A detailed analysis of the aspects of an individual's gait, such as joint kinematics, ground reaction forces, electrical activity of muscles, or energy requirements of walking provide insightful quantitative information. Unfortunately, such measurements often fail to reflect the activity level of an individual going about normal daily life and the activities accompanied therewith.

Long-term measures of physical activity can provide meaningful quantitative indicators of an individual's condition and physical levels. A number of devices are commercially available to measure physical activity of an individual over an extended period of time. Such devices can provide a time-based breakdown of data and capture changing patterns of activity. A limitation to these devices is that they may only provide raw data or a degree of the activity level of an individual based only on the one or two variables. As a result, the devices to not take into account different behavioral patterns of the individual and may incorrectly grade an individual's activity level.

SUMMARY

According to one or more aspects of the invention, a method is provided for quantifying activity levels of an individual within a predetermined time period which accurately and objectively measures and reports a single activity index representative of the degree of activity of an individual.

In a variation of a method according to the invention, a plurality of activity variables are measured from an individual during a predetermined time period and the activity variables are provided with minimum and maximum threshold values and a weighing factor. A subindex is calculated for each of the activity variables over the predetermined time period as a function of the minimum and maximum threshold values and the weighing factor. The sum of the subindexes is totaled and this sum represents a single activity index of an individual.

The aforesaid exemplary method of the invention may be incorporated in a personal activity level analysis system that may be embodied as a portable device. The portable device can accommodate, monitor and measure a wide variety of movements and activities of an individual. The device may include a plurality of acceleration measuring devices arranged for measuring activity variables within a predetermined time period. The device may also have a processor configured to execute the aforesaid exemplary method to yield an activity index representative of the activity level of an individual over a time period that the device is worn.

Other aspects and features of the invention will become apparent from the following drawings and detailed description.

BRIEF DESCRIPTION OF THE DRAWINGS

These and other features, aspects, and advantages of the present invention will become better understood with regard to the following description, appended claims, and accompanying drawings where:

FIGS. 2 and 3 are tables showing data and the activity indexes of individuals in accordance with an exemplary method of the present invention.

DETAILED DESCRIPTION OF VARIOUS EMBODIMENTS

A. Overview

Figure 1:
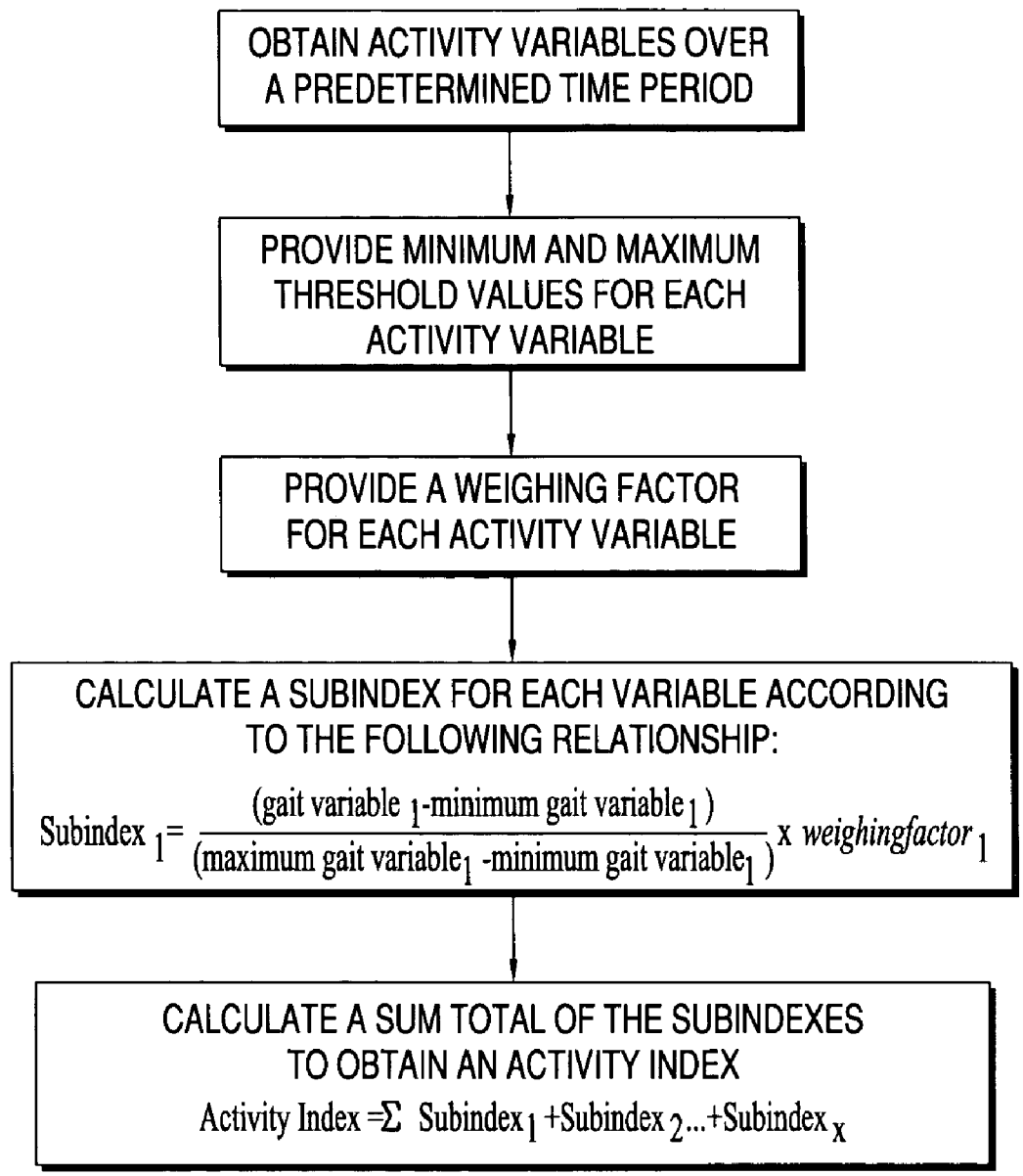
FIG. 1 is a flow diagram showing an exemplary method of the invention.

A better understanding of different embodiments of the invention may be had from the following description read in conjunction with the accompanying drawings in which like reference characters refer to like elements.

While the disclosure is susceptible to various modifications and alternative constructions, certain illustrative embodiments thereof are shown in the drawings and will be described below in detail. It should be understood, however, that there is no intention to limit the disclosure to the specific embodiments disclosed, but on the contrary, the intention is to cover all modifications, alternative constructions, combinations, and equivalents falling within the spirit and scope of the disclosure and defined by the appended claims.

It will be understood that, unless a term is expressly defined in this patent to possess a described meaning, there is no intent to limit the meaning of such term, either expressly or indirectly, beyond its plain or ordinary meaning.

Any element in a claim that does not explicitly state "means for" performing a specified function, or "step for" performing a specific function, is not to be interpreted as a "means" or "step" clause as specified in 35 U.S.C. § 112, paragraph 6.

B. Description

The methods and system of the present invention may be used for monitoring activity based behavior in an individual. Although the exemplary methods of the invention below refer to measuring and calculating an activity level related to an individual's ambulatory function, it should be understood that the exemplary methods may be applied to any condition which expresses itself in physical activity with discernible characteristics.

In an exemplary method of the invention shown in the flow chart of FIG. 1, one or more activity variables are measured from an individual during a predetermined time period. A measuring and processing device, as will be described in more detail below, may be employed to perform the exemplary method. Each of these activity variables is provided with minimum and maximum threshold values and a weighing factor. A subindex is calculated for each of the activity variables over the predetermined time period as a function of the minimum and maximum threshold values and the weighing factor. The sum of the subindexes is totaled and the sum represents an activity level of an individual.

According to this method, the subindex for each activity variable is calculated using the following relationship:

$$Subindex_1 = \frac{(\text{activity } variable_1 - \text{minimum activity } variable_1)}{(\text{maximum activity } variable_1 - \text{minimum activity } variable_1)} \times weighing factor_1$$

It follows that that the sum of the subindexes or activity level is calculated using the following relationship, where "x" is the last sub-index:

Activity Index=$\Sigma$Subindex$_1$+Subindex$_2$ . . . +Subindex$_x$

A determination of the activity level in an individual may be based on any number of ambulatory and gait characteristics. One ambulatory characteristic includes measuring the amount of time an individual is in an active class which is defined as the total time period the individual has ambulated without taking more than a predetermined streak of steps, for example a streak of less than 10 consecutive steps. Typically the active class occurs when an individual is moving around their home or office, or is engaged in activity requiring a minimal amount of steps. Another ambulatory characteristic includes measuring the amount of time an individual is in a locomotion class which is defined as the total time period the individual has taken more than a predetermined streak of steps, for example a streak of more than 10 consecutive steps.

When an individual has entered the locomotion class, the individual has initiated a walking streak and the amount of walking streaks may be tabulated and analyzed. In conjunction with the walking streak, another measurement is the maximum sustained walking speed which is measured over a series of consecutive steps, for example 10 consecutive steps. In the context of the present application, two steps are commonly referred to as a stride.

In accordance with the invention, the activity variables used to determine the activity level of an individual preferably include gait variables such as a total number of steps or strides during the predetermined time period, a total distance traveled, a mean gait velocity, an average cadence preferably measured in steps or strides per minute, a maximum sustained gait velocity, a maximum period of locomotion, a maximum consecutive distance traveled, number of periods of locomotion, a total time spent in the active and locomotion classes. Other variables that may be used include other gait parameters such as the instantaneous, average, maximum or minimum elevation of an individual's foot above the ground, range of motion measured as the degree the foot enters the sagital plane, and the symmetry of gait measured as the difference between a degree of motion between the right and left feet. Moreover, behavioral variables may be used such as a total time the individual spent running, the number of steps during the total time spent running, the number of steps spent when in the active class, a total time an individual wears a prosthesis or an orthosis, a longest period of physical activity within the predetermined time period, a total number activities of an individual such as standing, sitting, walking, running, bicycling, climbing stairs and other ascertainable activities relevant to determining an activity level. It will be understood that the invention is not limited to the aforementioned variables, and any number of suitable variables may be used that will enable one to determine the activity level of an individual.

According to the invention, the minimum variable threshold value represents about a lowest level in the range of the respective activity variable before such a variable begins to influence the activity index. The maximum variable threshold value conversely represents about a highest level of the range of the respective activity variable at which point it ceases to influence the activity index. The minimum and maximum threshold values are generally based on experimental data, and usually are not specific to a certain individual. Such minimum and maximum threshold values may be varied over time and accordingly may be modified.

The weighing factor controls how much each activity variable will influence the activity index and a relatively high weighing factor will have a greater effect on the activity index than a relatively low weighing factor. The weighing factors may vary from activity variable to activity variable. For example, in the event an individual or healthcare professional desires to increase the effect of one of such activity variables, the weighing factor could likewise be increased to reflect the influence of the specific activity variable on the projected activity index of an individual.

The activity index may be compared to a scale to determine the activity index of an individual. More specifically, the scale may be divided into ranges that represent the activity levels that an individual may represent and may be used by a healthcare professional to determine a type of shoe, prosthesis or orthosis component that may be appropriate for an individual. For example, in the case an individual is an amputee, a relatively high activity index level may result in the selection of a prosthetic suspension sleeve that is adapted for active amputees that experience greater stress on the residual limb and require superior stability and intimacy of fit to lead an active lifestyle. Alternatively, in the case an individual requires an orthosis, a lower activity index level may result in the selection of a less rigid orthosis that may provide more comfort than stability.

As shown in FIGS. 2 and 3, sample data is presented showing the activity levels of above the knee amputees in FIG. 2 and below the knee amputees in FIG. 3. In observing FIG. 2, it is readily apparent that the activity index for each individual varies and the activity level of each individual can be classified according to their activity index in one of at least three activity categories: low activity, medium activity and high activity. Similarly, in FIG. 3, each individual is classified on the basis of their activity index in one of the three activity level categories discussed in relation to FIG. 2.

The aforesaid exemplary method of the invention may be incorporated into a measuring and processing device. Measuring and processing devices such as motion analysis systems are well known in the art, an example of one being disclosed in U.S. Pat. No. 6,513,381 incorporated herein by reference.

As discussed in U.S. Pat. No. 6,513,381, a motion analysis system may include at least a pair of accelerometers and a tilt sensor mounted in fixed relation to a datum plane defining surface such as the sole of a shoe. The motion system also includes a processor arranged to determine angular acceleration values based on the measurements made by the accelerometers and to extract kinematical parameters such as linear and rotational acceleration, velocity and position from the accelerometers. From the kinematical parameters, the motion analysis system can obtain the activity variables, such as those described above, and further perform the aforesaid calculations to obtain an activity index.

Preferably, the motion analysis system is configured as a portable unit that can be easily worn by an individual along their leg, ankle or foot. In an embodiment of the invention illustrated in FIG. 4, the portable unit 10 is to be worn on a lower limb or leg prosthesis 12 to obtain data regarding the activity levels of the individual wearing the prosthesis. In this embodiment, the motion analysis system is configured to detect the strides of the individual and preferably is configured to obtain data of the individual over at least one day, preferably six days, and calculating such data to obtain the activity index of the individual.

Figure 4:
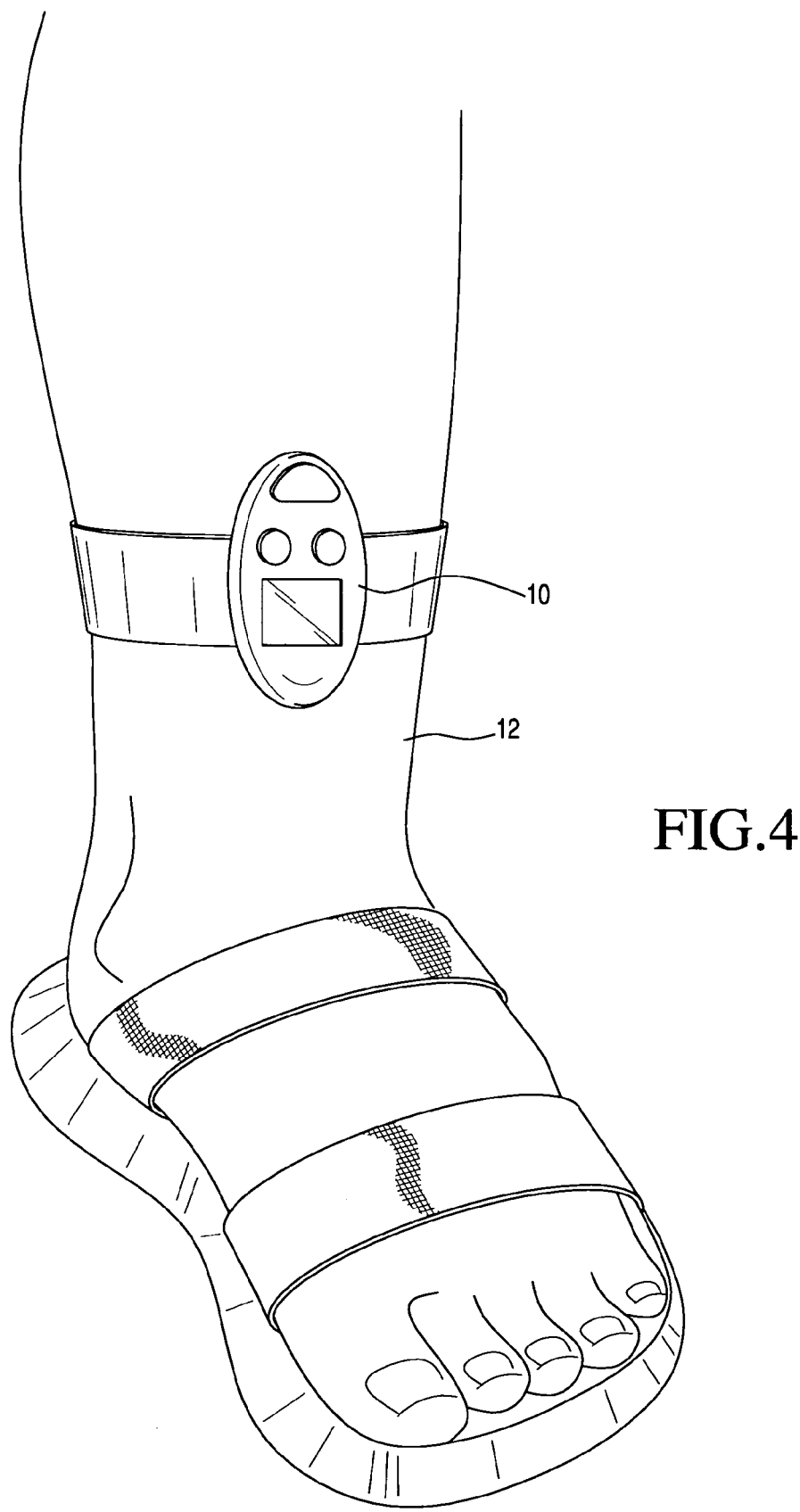
FIG. 4 is a perspective view showing a portable device on a leg of an individual for measuring an activity index.

As shown in FIG. 4, the portable unit 10 is preferably worn on the anterior side of a leg 12 or a leg prosthesis, approximately 20 cm above the ground. It will be noted, however, that the accelerometers and processor of the portable unit may be modified so that the portable unit 10 can be attached to other locations of the body such as along the thigh, waist or arms of the individual, and further configured to obtain data from the individual corresponding to movement related to such locations. Moreover, the portable unit is not limited to being arranged at the described distance above the ground, but may be modified accordingly to allow for the placement of such unit at other body locations.

It will be understood that the above described features of the invention are illustrative in nature, and that modifications thereof may occur to those skilled in the art. Accordingly, this invention is not to be regarded as limited to the features disclosed herein, but is to be limited only as defined in the appended claims.

I claim:

1. A method for quantifying an activity level of an individual within a predetermined time period with a measuring and processing device based on a plurality of activity variables, said measuring and processing device storing for each of said plurality of activity variables a minimum activity variable corresponding to a generally minimum threshold level of the activity variable, a maximum activity variable corresponding to a generally maximum threshold level of the activity variable, and a weighing factor, the method comprising the steps of:

measuring the plurality of activity variables of an individual over said time period with said measuring and processing device;

calculating with said measuring and processing device a subindex for each of said activity variables using the following relationship $$\text{Subindex} = \frac{(\text{activity variable} - \text{minimum activity variable})}{(\text{maximum activity variable} - \text{minimum activity variable})} \times \text{weighing factor}$$

calculating with said measuring and processing device the sum of said subindexes to determine an activity index corresponding to an activity level of an individual.

2. The method according to claim 1, wherein the activity variables relate to the gait and ambulation of an individual and comprise at least one of the following variables: a total number of steps, a total distance traveled, an average gait speed, an average cadence, a maximum sustained gait speed, a maximum period of locomotion, a maximum consecutive distance traveled, and combinations and sum totals thereof.

3. The method according to claim 1, wherein the weighing factor is selected on the basis of the influence of the respective activity variable on the activity index.

4. The method according to claim 3, further comprising comparing the activity index to a scale to determine the activity level of an individual.

5. A method for quantifying activity levels of an individual within a predetermined time period with a processing device, the processing device storing minimum and maximum threshold values and a weighing factor associated with a set of activity variables of an individual, the method comprising the steps of:

measuring a plurality of activity variables of an individual over said predetermined time period;

calculating in the processing device a subindex for each of said activity variables as a function of the minimum and maximum threshold values and the weighing factor; and calculating in the processing device a sum of said activity variables to determine an activity index corresponding to an activity level of an individual.

6. The method according to claim 5, wherein the activity variables relate to the gait and ambulation of an individual and comprise at least one of the following variables: a total number of steps, a total distance traveled, an average gait speed, an average cadence, a maximum sustained gait speed, a maximum period of locomotion, a maximum consecutive distance traveled, and combinations and sum totals thereof.

7. The method according to claim 5, wherein the weighing factor is selected on the basis of the influence of the respective activity variable on the activity index.

8. The method according to claim 5, further comprising comparing the activity index to a scale to determine the activity level of an individual.

9. A personal activity level analysis system, comprising:

at least one measuring device arranged for measuring activity information of an individual within a predetermined time period; and a processor configured to determine a plurality of activity variables from the activity information obtained from the measuring devices within the predetermined time period, said processor storing minimum and maximum threshold values and a weighing factor for each of said activity variables, said processor arranged to calculate a subindex for each of said activity variables as a function of the minimum and maximum threshold values and the weighing factor, and said processor configured to determine an activity index from a sum of the subindexes of the activity variables.

10. The personal activity level analysis system according to claim 9, wherein the activity variables relate to the gait and ambulation of an individual.

11. A method for quantifying activity levels of an individual within a predetermined time period, the method comprising the steps of:

measuring a plurality of activity variables of an individual during said predetermined time period;

providing said plurality of activity variables with minimum and maximum threshold values and a weighing factor;

calculating a subindex for each of said activity variables as a function of the minimum and maximum threshold values and the weighing factor; and calculating a sum of said activity variables to determine an activity index corresponding to an activity level of an individual.

* * * * *